United States Patent
Ali et al.

(10) Patent No.: US 7,041,279 B1
(45) Date of Patent: May 9, 2006

(54) METHOD AND PRODUCT FOR MITIGATING PET MALODORS

(75) Inventors: Sheila E. Ali, San Ramon, CA (US); David Peterson, Pleasanton, CA (US); Gregory M. Piché, Dublin, CA (US); Roger V. Lee, Fremont, CA (US)

(73) Assignee: The Clorox Company, Oakland, CA (US)

( * ) Notice: Subject to any disclaimer, the term of this patent is extended or adjusted under 35 U.S.C. 154(b) by 0 days.

(21) Appl. No.: 09/469,575

(22) Filed: Dec. 22, 1999

Related U.S. Application Data

(60) Provisional application No. 60/162,808, filed on Nov. 1, 1999.

(51) Int. Cl.
*A61L 9/00* (2006.01)
*A61L 11/00* (2006.01)
*A61L 9/01* (2006.01)
*A61L 9/02* (2006.01)
*A61L 9/14* (2006.01)

(52) U.S. Cl. .................... 424/76.6; 424/76.1; 424/76.2

(58) Field of Classification Search ............... 424/76.4, 424/76.6, 76.5, 76.2, 76.1
See application file for complete search history.

(56) References Cited

U.S. PATENT DOCUMENTS

| | | | |
|---|---|---|---|
| 3,567,118 A | 3/1971 | Shepherd ...................... 239/6 |
| 4,048,369 A | 9/1977 | Johnson ..................... 428/262 |
| 4,184,985 A | 1/1980 | Scheuermann et al. ..... 252/522 |
| 4,540,721 A | 9/1985 | Staller ......................... 523/102 |
| 4,606,842 A | 8/1986 | Keyes et al. ........... 252/174.23 |
| 4,934,609 A | 6/1990 | Lindauer et al. ............... 241/3 |
| 4,938,416 A | 7/1990 | Bertrand et al. ............... 239/1 |
| 5,126,068 A | 6/1992 | Burke et al. .......... 252/174.21 |
| 5,183,655 A * | 2/1993 | Stanislowski et al. ..... 424/76.6 |
| 5,359,961 A * | 11/1994 | Goss et al. .................. 119/173 |
| 5,380,707 A | 1/1995 | Barr et al. .................... 512/17 |
| 5,516,830 A * | 5/1996 | Nachtman et al. |
| 5,593,670 A | 1/1997 | Trinh et al. ................. 424/76.1 |
| 5,663,134 A | 9/1997 | Trinh et al. ................. 510/406 |
| 5,783,544 A | 7/1998 | Trinh et al. ................. 510/293 |
| 5,939,060 A | 8/1999 | Trinh et al. ................. 424/76.4 |
| 5,992,251 A * | 11/1999 | Grieger et al. ............. 73/866.5 |
| 5,992,351 A * | 11/1999 | Jenkins |
| 6,454,876 B1 * | 9/2002 | Ochomogo et al. ........... 134/42 |

FOREIGN PATENT DOCUMENTS

| | | |
|---|---|---|
| GB | 1458836 | 12/1976 |
| GB | 1458837 | 12/1976 |
| GB | 2327882 | 2/1999 |
| WO | WO 96/04938 | 2/1996 |
| WO | WO 97/34986 | 9/1997 |

* cited by examiner

*Primary Examiner*—Carlos A. Azpuru
*Assistant Examiner*—David Vanik
(74) *Attorney, Agent, or Firm*—Ann Lee; Stephen J. Sand

(57) ABSTRACT

The invention provides a method and product for mitigating or eliminating pet malodor(s) with an aqueous liquid deodorizing composition, the composition containing about at least 0.01% to about 10% of an dialkali metal tetraborate n-hydrate (with n being an integer from 0 to 10), 0.1–3% water soluble/dispersible polymer, 1–25% water soluble/dispersible volatile solvent, at least 75% water.

6 Claims, 3 Drawing Sheets

Cat Spray Odor Reduction

METHOD AND PRODUCT FOR MITIGATING PET MALODORS

RELATED APPLICATIONS

This is a continuation-in-part of Provisional Application No. 60/162,808, filed Nov. 1, 1999.

BACKGROUND OF THE INVENTION

1. Field of the Invention

The invention relates to a method and product for mitigating or eliminating pet malodors, particularly those which arise from feline urine. The method provides for the contacting of the malodor(s) with an aqueous liquid deodorizing composition, the composition containing about at least 0.01% to about 10% of an alkali metal tetraborate n-hydrate (with n being an integer from 0 to 10), 0.1–3% water soluble/dispersible polymer, 1–25% water soluble/dispersible volatile solvent, at least 75% water and various aesthetic and functional additives.

2. Brief Statement of the Related Art

One of the most common and distressing household odors is caused by pets, such as cats, who must void or eliminate in the home in discrete areas, such as litter boxes or other containment devices. However, since replacement or replenishment of the litter box is left to individual discretion, some home environments may succumb to a perceived higher level of malodor than others. Additionally, the individual pet may, depending on its health and the amount of water and/or feed it intakes, produce more liquid and solid wastes than others. Further, some pets because of instinctive need or other such motivation, "mark" or spray surfaces outside of the litter box, perhaps as a means of establishing territory or some other behavioral idiosyncracy. In all such events, there is thus a need for a deodorizer or malodor mitigator which is specially formulated to deal with these particular malodors.

Stanislowski et al., U.S. Pat. No. 5,183,655 (of common assignment and incorporated herein by reference), discloses and claims an animal waste deodorizer comprising a mixture of pine oil and a borate-based compound selected from polyborate, borax and a boric acid/borax mixture, carried in a liquid dispersion. Stanislowski, however, does not teach, disclose or suggest the presence of a water soluble/dispersible polymer in its deodorizer.

On the other hand, there are many references to animal litters which are pretreated with boron-containing compounds, especially boric acid, which have been identified as effective additives. These are discussed in, for example, Ratcliff et al., U.S. Pat. Nos. 4,949,672 and 5,094,190, Jenkins et al., U.S. Pat. No. 5,176,108, and Stanislowski et al., U.S. Pat. Nos. 5,018,482, 5,135,743 and 5,183,655, all of which are of common assignment and incorporated herein by reference thereto. Of course, these types of litters cannot suppress malodors indefinitely. Moreover, even the best animal litter cannot guarantee that the household pet, especially the domesticated feline, will be adequately trained to use the litter box or other containment means, will be sufficiently accurate in its private duties to make sure that its wastes are retained in the litter box, or will not be behaviorally motivated to mark or spray other surfaces in the household.

There are presently some liquid household malodor counteractants, such as aerosols and spray-dispensed liquid compositions. None, however, appear to disclose, teach or suggest that borax in a liquid deodorizing composition is especially effective at mitigating or eliminating pet malodors, particularly those which arise from feline urine.

SUMMARY AND OBJECTS OF THE INVENTION

The invention provides a method and product for contacting of pet malodor(s) with an aqueous liquid deodorizing composition, the composition containing about at least 0.01% to about 10% of an alkali metal tetraborate n-hydrate (with n being an integer from 0 to 10), 0.1–3% water soluble/dispersible polymer, 1–25% water soluble/dispersible volatile solvent, at least 75% water. In alternative embodiments, various aesthetic and functional additives may be added in low levels, such as surfactants/emulsifiers, fragrances, and preservatives.

It is therefore an object of this invention to provide a method for the counteracting of pet malodors by contacting them with an aqueous liquid deodorizing composition.

It is another object of this invention to provide a convenient product for mitigating or eliminating pet malodors, particularly those caused by domestic felines.

It is a further object of this invention to provide a trigger sprayer, pump sprayer, aerosol or other consumer-friendly means for delivering the malodor counteractant of this invention.

It is also an object of this invention to provide a long lasting means for malodor control, especially when compared to what is presently commercially available.

DETAILED DESCRIPTION OF THE INVENTION

Figure 1:
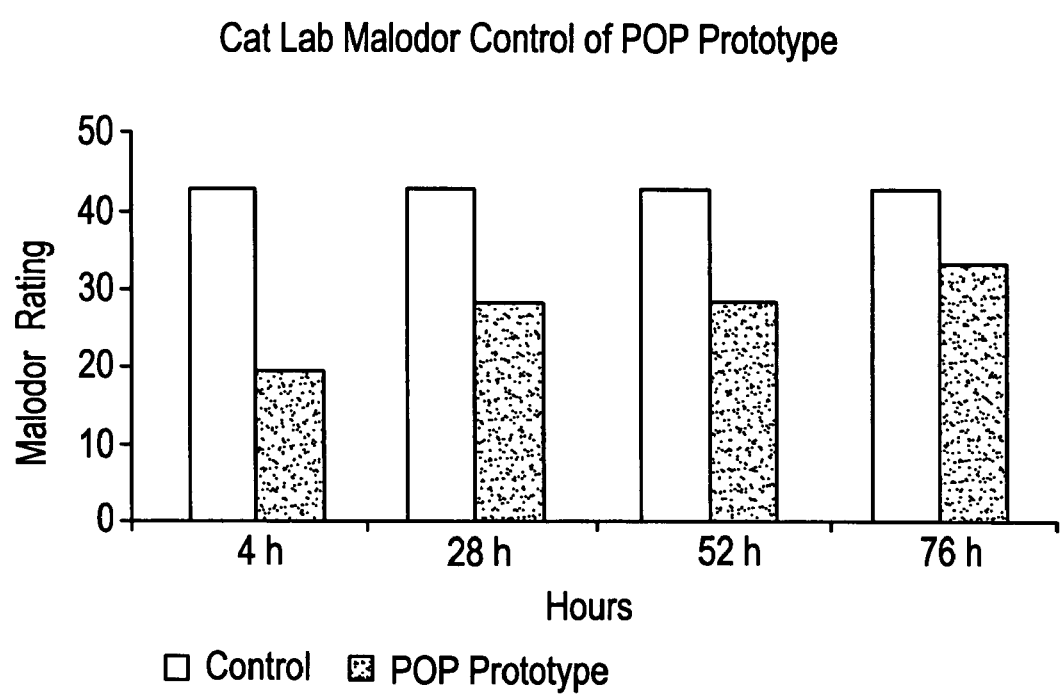
FIG. 1 is a bar graph depicting the performance of the inventive malodor counteractant versus a control.

The invention provides a method and product for contacting of pet malodor(s) with an aqueous liquid deodorizing composition, the composition containing about at least 0.5% to about 5% of an alkali metal tetraborate n-hydrate (with n being an integer from 0 to 10), 0.1–3% water soluble/dispersible polymer, 1–25% water soluble/dispersible volatile solvent, at least 75% water. In alternative embodiments, various aesthetic and functional additives may be added in low levels, such as surfactants/emulsifiers, fragrances, and preservatives.

The present invention provides a method and product for contacting of pet malodor(s) with an aqueous liquid deodorizing composition in which ammonia formation due to decomposition of urea present in animal waste may be affected by one or more mechanisms: (1) Urease Inhibition. Urease is an enzyme which is produced by many bacteria and other microflora. Urease acts as a catalyst to break down urea into ammonia via the following chemical pathway:

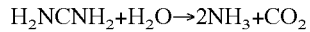

$H_2NCNH_2 + H_2O \rightarrow 2NH_3 + CO_2$

Control of urease, via competition, denaturation, or enzyme poisoning, would therefore significantly reduce the formation of ammonia. (2) Bacterial Inhibition. As previously discussed, bacteria and other microflora appear to be sources for urease. Thus, reduction of bacteria through antimicrobial action of the odor control agents would also significantly control odor formation.

It has been surprisingly discovered that a dramatic reduction in malodor formation caused by domestic animals occurs if the animal's liquid waste is contacted with the inventive aqueous liquid deodorizing composition, the composition containing about at least 0.5% to about 5% of an alkali metal tetraborate n-hydrate (with n being an integer from 0 to 10), 0.1–3% water soluble/dispersible polymer, 1–20% water soluble/dispersible volatile solvent, at least 75% water.

In the application, effective amounts are generally those amounts listed as the ranges or levels of ingredients in the descriptions which follow here to. Unless otherwise stated, amounts listed in percentage ("%'s") are in weight percent of the composition, unless otherwise noted.

The ingredients constituting the novel liquid pet malodor mitigating composition are described hereinbelow.

1. Boron-Based Odor Control Agent:

Borax, or, more accurately, di-alkali metal tetraborate n-hydrate (preferably, $Na_2B_4O_7 \times nH_2O$, where n=0–10, most preferably, 4, 5 or 10, although anhydrous borax is possible), is the preferred compound for use in the invention. The alkali metal counterion may be selected from sodium, potassium or lithium, or a combination thereof. Borax decahydrate is the most commonly found form of borax and is the compound assumed when one discusses borax. Borax pentahydrate is another preferred compound. Other boron-based compounds potentially suitable for use are disclosed in *Kirk-Othmer, Encyclopedia of Chemical Technology*, 3rd Ed., Vol. 4, pp. 67–109 (1978), said pages being incorporated herein by reference. Borax can be obtained from such vendors as U.S. Borax and North American Borax.

Borax appears to provide multiple benefits in odor control by: (1) acting as a urease inhibitor, which controls odors by preventing enzymatic breakdown of urea; (2) having bacteriostatic properties, which appear to help control odor by controlling the growth of bacteria which are responsible for production of the urease enzymes.

An alternative odor control animal litter additive is boric acid. See, *Kirk-Othmer, Encyclopedia Chemical Technology*, 3rd Ed., Vol. 4, pp. 71–77 (1978), incorporated herein by reference. Boric acid has the structure $H_3BO_3$. Boric acid is available from such suppliers as Kerr-McGee Corporation. Polyborate, tetraboric acid, sodium metaborate and other forms of boron are also appropriate alternative materials.

An odor controlling effective amount is defined as at least about 0.01% equivalent boron, more preferably at least greater than 0.03%. The preferred range varies from about 0.02 to about 10%, by weight of the composition. The more preferable range is about 0.02 to 5% by weight of the composition. Those skilled in the art will adjust the compositional levels to ensure effective odor control and cost effectiveness.

In the following discussion, percent boron is defined as the amount of atomic boron delivered in wt. %. Percent boron is determined by calculating the amount of atomic boron in a boron-containing compound. So, for boric acid, borax decahydrate and borax pentahydrate, percent boron is:

$$1 \text{ g boric acid}^1 \ (10.81 \text{ g B}^2) = 0.1748 \times 100\% = 17.48\%$$

$$61.84 \text{ g boric acid}$$

$$1 \text{ g borax}^3 \ (43.24 \text{ g B}^2) = 0.1134 \times 100\% = 11.34\%$$

$$381.37 \text{ g borax}$$

$$1 \text{ g borax}^4 \ (43.24 \text{ g B}^2) = 0.1484 \times 100\% = 14.8\%$$

$$291.37 \text{ g borax}$$

[1] Molecular weight of boric acid ($H_3BO_3$) is 61.84.

[2] Atomic weight of boron is 10.81. In boric acid, there is only one atom of boron; in borax, there are four.

[3] Molecular weight of borax ($Na_2B_4O_7 \times 10H_2O$) is 381.37, assuming borax decahydrate.

[4] Molecular weight of borax ($Na_2B_4O_7 \times 5 H_2O$) is 291.37, assuming borax pentahydrate 2. The Water Soluble/Dispersible Polymer(s)

The polymer is another key component of the invention. It is necessary to provide substantivity via a transparent to slightly visible residue or film which results after application of the inventive liquid composition to a surface.

The polymer is generally speaking a water soluble to dispersible polymer having a molecular weight of generally below 2,000,000 daltons. The polymers will also be not damaging to fabrics, carpets, and other soft surfaces. They should have enough tack or stickiness, when applied and dried, to provide a matrix in which the boron additive and materials and the animal waste may be entrapped, but not so much that to the human touch the film or residue feels or imparts an obvious sticky feel. Preferably, the polymer will also not itself have an obvious or offensive odor, although that attribute can be mitigated by judicious selection of fragrance.

Examples of suitable classes of polymers include:

a. Polysaccharides

Suitable polymers may comprise polysaccharide polymers, which include substituted cellulose materials like carboxymethylcellulose, ethyl cellulose, hydroxyethylcellulose, hydroxypropylcellulose, hydroxymethylcellulose, succinoglycan and naturally occurring polysaccharide polymers like xanthan gum, guar gum, locust bean gum, tragacanth gum or derivatives thereof. Particularly useful polysaccharides are xanthan gum and derivatives thereof. Some of these are thickeners which may have too much tack, from a performance and aesthetic standpoint. Additional suitable polysaccharide polymers may include sodium caseinate and gelatin. Other suitable polysaccharide polymers may include cationic derivatives, such as the cationic cellulose ether, Polymer JR.

b. Polycarboxylates

Polycarboxylates can also be used which contain amounts of nonionizable monomers, such as ethylene and other simple olefins, styrene, alpha-methylstyrene, methyl, ethyl and $C_3$ to $C_8$ alkyl acrylates and methacrylates, isobornyl methacrylate, acrylamide, hydroxyethyl acrylate and methacrylate, hydroxypropyl acrylate and methacrylate, N-vinyl pyrrolidone, butadiene, isoprene, vinyl halides such as vinyl chloride and vinylidine chloride, alkyl maleates, alkyl fumarates. Other suitable polymers include other polycarboxylates, such as homopolymers and copolymers of monomeric units selected from the group consisting of unsaturated carboxylic acids such as acrylic acid, methacrylic acid, polycarboxylic acids, sulfonic acids, phosphonic acids and mixtures thereof. Copolymerization of the above monomeric units among them or with other comonomers such as maleic anhydride, ethylene or propylene are also suitable.

c. Polystyrenesulfonates

Other suitable polymers are polystyrenesulfonates such as Flexan 130 and Versa TL501 from National Starch and Chemical. Polystyrenesulfonates are also useful as copolymers, for example Versa TL-4 also from National Starch and Chemical.

d. Acrylate Polymers

Other suitable polymers are acrylic emulsion polymers used as floor polish coatings. These are generally copolymers of one or more acidic monomers, such as acrylic acid, methacrylic acid or maleic anhydride, with at least one other ethylenically unsaturated monomer selected from a group consisting of ethylene and other simple olefins, styrene, alpha-methylstyrene, methyl, ethyl and $C_3$ to $C_8$ alkyl acrylates and methacrylates, isobornyl methacrylate, acrylamide, hydroxyethyl acrylate and methacrylate, hydroxypropyl acrylate and methacrylate, N-vinyl pyrrolidone, butadiene, isoprene, vinyl halides such as vinyl chloride and vinylidine chloride, alkyl maleates, alkyl fumarates, fumaric acid, maleic acid, itaconic acid, and the like. It is also frequently desirable to include minor amounts of other functional monomers, such as acetoacetoxy methacrylate or other acetoacetate monomers and divinyl or polyvinyl monomers, such as glycol polyacrylates, allyl methacrylate, divinyl benzene and the like. The preferred polymers have an acid number from about 75 to about 500 and a number average molecular weight of about 500 to about 20,000. These polymers may also be crosslinked with metal ions or modified for crosslinking with silane functionality as described, for example, in U.S. Pat. No. 5,428,107. Examples of such acrylic emulsion polymers include those available under the Rhoplex tradename from Rohm & Haas, such as Rhoplex AC-33, Rhoplex B-924, and Rhoplex MC-76. There are also polymers from Alco, such as Balance CR, Balance 47 and Balance 055. There are also polymers from National Starch and Chemical, such as Amaze, Flexan and Balance CR, Balance 47 and Balance 055. Another preferred polymer is Carboset by B.F. Goodrich. Other suitable polymers are copolymers of acrylic and/or methacrylic acid with acrylate and methacrylate esters. For example, a copolymer of 51% methyl methacrylate, 31% butyl acrylate, and 18% acrylic acid is available from Rohm & Haas as Emulsion Polymer E-1250. Additionally, there are acrylates from Rohm and Haas, namely, Acusol, such as Acusol 445, and the like. See also Keyes et al., U.S. Pat. No. 4,606,842, incorporated herein by reference.

Other suitable polymers may include cationic acrylic water soluble polymers that are copolymers of cationic quaternized acrylates, methacrylates, acrylamides, and methacrylamides, for example trimethylammoniumpropylmethacrylate, and acrylamide or acrylonitrile.

e. Polyethyleneimines

Other suitable polymers are polyethyleneimines and copolymers with other polyalkyleneimines. These aminofunctional polymers can also be modified by ethoxylation and propoxylation. These amino-functional polymers can also be quanternized with methyl groups or oxidized to amine oxides.

f. Polyvinylpyrrolidones

Other suitable polymers include vinylpyrrolidone homopolymers and copolymers. Suitable vinylpyrrolidone homopolymers have an average molecular weight of from 1,000 to 100,000,000, preferably from 2,000 to 10,000,000, more preferably from 5,000 to 1,000,000, and most preferably from 30,000 to 700,000. Suitable vinyl pyrrolidone homopolymers are commercially available from ISP Corporation, Wayne, N.J. under the product names PVP K-15 (average molecular weight of 8,000), PVP K30 (average molecular weight of 38,000), PVP K-60 (average molecular weight of 216,000), PVP K-90 (average molecular weight of 630,000), and PVP K-120 (average molecular weight of 2,900,000). Suitable copolymers of vinylpyrrolidone include copolymers of N-vinylpyrrolidone with one or more alkylenically unsaturated monomers. Suitable alkylenically unsaturated monomers include unsaturated dicarboxylic acids such as maleic acid, chloromaleic acid, fumaric acid, itaconic acid, citraconic acid, phenylmaleic acid, aconitic acid, acrylic acid, methacrylic acid, N-vinylimidazole, vinylcaprolactam, butene, hexadecene, and vinyl acetate. Any of the esters and amides of the unsaturated acids may be employed, for example, methyl acrylate, ethylacrylate, acrylamide, methacryamide, dimethylaminoethylmethacrylate, dimethylamino-propylmethacrylamide, trimethylammoniumethylmethacrylate, and trimethylammoniumpropylmethacrylamide. Other suitable alkylenically unsaturated monomers include aromatic monomers such as styrene, sulphonated styrene, alpha-methylstyrene, vinyltoluene, t-butylstyrene and others. Copolymers of vinylpyrrolidone with vinyl acetate are commercially available under the trade name PVP/VA from ISP Corporation. Copolymers of vinylpyrrolidone with alpha-olefins are available, for example, as P-904 from ISP Corporation. Copolymers of vinylpyrrolidone with dimethylaminoethylmethacrylate are available, for example, as Copolymer 958 from ISP Corporation. Copolymers of vinylpyrrolidone with trimethylammoniumethylmethacrylate are available, for example, as Gafquat 734 from ISP Corporation. Copolymers of vinylpyrrolidone with trimethylammoniumpropylmethacrylamide are available, for example, as Gafquat HS-100 from ISP Corporation. Copolymers of vinylpyrrolidone with styrene are available, for example, as Polectron 430 from ISP Corporation. Copolymers of vinylpyrrolidone with acrylic acid are available, for example, as Polymer ACP 1005 (25% vinylpyrrolidone/75% acrylic acid) from ISP Corporation.

g. Methylvinyl Ether

Other suitable polymers include methylvinylether homopolymers and copoymers. Preferred copolymers are those with maleic anhydride. These copolymers can be hydrolyzed to the diacid or derivatized as the monoalkyl ester. For example, the n-butyl ester is available as Gantrez ES-425 from ISP Corporation.

h. Polyvinyl Alcohols

Other suitable polymers include polyvinyl alcohols. Preferably, polyvinyl alcohols which are at least 80.0%, preferably 88–99.9%, and most preferably 99.0–99.8% hydrolyzed are used. For example, the polyvinyl alcohol, Elvanol 71-30 is available from E. I. DuPont de Nemours and Company, Wilmington, Del.

i. Polyethylene Glycols

Yet other feasible polymers may be polyethylene glycols, such as disclosed in Baker et al., U.S. Pat. No. 4,690,779, incorporated herein by reference.

Mixtures of any of the foregoing polymers may be possible or desirable. The hydrophilic polymer or polymers are present at a level of about 0.1–3% of the liquid malodor counteractant.

3. The Volatile Organic Solvent(s)

The solvents useful in this invention are organic solvents with a vapor pressure of at least 0.001 mm Hg at 25° C. and soluble to the extent of at least 1 g/100 ml water. The upper limit of vapor pressure appears to be about 100 mm Hg at 25° C. Vapor pressure is a useful measure for determining the applicability of the given solvent, since one would select a solvent which will volatilize sufficiently so as to leave no visible residue. The organic solvent of the invention is preferably selected from $C_{1-6}$ alkanol, $C_{1-24}$ alkylene glycol ether, and mixtures thereof. The $C_{1-6}$ alkanol solvents are preferred for use. The alkanol can be selected from methanol, ethanol, n-propanol, isopropanol, butanol, pentanol, hexanol, their various positional isomers, and mixtures of the foregoing. In the invention, it has been found most preferable to use ethanol, which has particularly good volatilization and solubilization characteristics. It may also be possible to utilize in addition to, or in place of, said alkanols, the diols such as methylene, ethylene, propylene and butylene glycols, and mixtures thereof. Other solvents, such as amines, ketones, ethers, hydrocarbons and halides may be useful. Other examples of solvents can be found in *Kirk-Othmer, Encyclopedia of Chemical Technology* 3rd, Vol. 21, pp. 377–401 (1983), incorporated by reference herein.

The alkylene glycol ether solvents can include ethylene glycol monobutyl ether, ethylene glycol monopropyl ether, propylene glycol monopropyl ether, propylene glycol monobutyl ether, and mixtures thereof.

It is preferred to limit the total amount of solvent to no more than 25%, more preferably no more than 15%, and most preferably, no more than 10%, of the aqueous liquid deodorizing formulation. Moreover, in some of the compositions of this invention, no solvent may be present. A preferred range is about 1–15%.

On the other hand, in some of the embodiments of the invention, an aerosol delivery is preferred. In such case, a propellant, such as a hydrocarbon blend (e.g., propane/isobutene), dimethyl ether, or other compressible gases, or, in the case of non-compressible gases, carbon dioxide, is included. When counted against the solvent level, the propellant will actually raise the solvent level to a minimum of about at least 15%, more preferably at least 25%, of the composition. The water level would be decreased correspondingly.

4. Water

The third principal ingredient is water, which should be present at a level of at least about 75%, more preferably at least about 80%, and most preferably, at least about 85%. Deionized water is most preferred. Water forms the predominant, continuous phase in which the ingredients are solubilized or dispersed.

In those applications where an aerosol form is desired and water forms the predominant, continuous phase, the water should be present at a level of at least about 55% to allow for use of propellant. However, the formula delivered to the surface after volatilization of the propellant will be essentially that described above, including water present at a level of at least 75%, more preferably at least about 80%, and most preferably, at least about 85%.

5. Aesthetic/Functional Additives

Various desirable Actives include:

a. Surfactants

The surfactants used in the invention may be one or more nonionic surfactants which have a HLB of about 3–16. For a further discussion of HLB measurements, one should consult Popiel, *Introduction to Colloid Science* (1978), pp. 43–44 and Gerhartz, *Ullmann's Encyclopedia of Industrial Chemistry*, 5th Ed., Vol. A9 (1985), pp. 322–23, both of which are incorporated by reference thereto.

Surfactants may be selected from linear and branched alkoxylated alcohols, alkoxylated alkylphenols and alkylpolyglycosides, among others. The alkoxylated alcohols include ethoxylated, propoxylated, and ethoxylated and propoxylated $C_{5-20}$ alcohols, with about 1–5 moles of ethylene oxide, or about 1–5 moles of propylene oxide, or 1–5 and 1–5 moles of ethylene oxide and propylene oxide, respectively, per mole of alcohol. There are a wide variety of products from numerous manufacturers, such as the Neodol series from Texaco Chemical Co., to wit, Neodol 25-3, a linear $C_{12-15}$ alcohol ethoxylate with 3 moles of ethylene oxide ("EO") per mole of alcohol, HLB of 7.8, and Neodol 91-2.5, a linear $C_{9-11}$ alcohol ethoxylate with 2.5 moles of EO; Alfonic 1412-40, a $C_{12-14}$ ethoxylated alcohol with 3 moles of EO from Conoco; Surfonic L12-2.6, a $C_{10-12}$ ethoxylated alcohol with 3 moles of EO, and Surfonic L24-3, a $C_{12-14}$ ethoxylated alcohol with 3 moles of EO from Huntsman Chemical; and Tergitol 25-L-3, a $C_{12-15}$ ethoxylated alcohol with 3 moles of EO, from Union Carbide. The secondary ethoxylated alcohols include Tergitol 15-S-3, a $C_{11-15}$ secondary ethoxylated alcohol, with 3 moles of EO, from Union Carbide.

The branched surfactants, especially preferred of which are tridecyl ethers, include Trycol TDA-3, a tridecyl ether with 3 moles of EO, from Henkel KGaA (formerly, Emery), and Macol TD 3, a tridecyl ether with 3 moles of EO, from PPG Industries. See, also, *McCutcheon's Emulsifiers and Detergents*, 1987. The sparingly soluble nonionic surfactant can also be selected from alkoxylated alkylphenols, such as: Macol NP-4, an ethoxylated nonylphenol with 4 moles of EO, and an HLB of 8.8, from PPG; Triton N-57, an ethoxylated nonylphenol with an HLB of 10.0, Triton N-42, an ethoxylated nonylphenol with an HLB of 9.1, both from Rohm & Haas Co.; and Igepal CO-520, with an HLB of 10.0, an ethoxylated nonylphenol from GAF Chemicals Corp.; Alkasurf NP-5, with an HLB of 10.0, and Alkasurf NP-4, with an HLB of 9.0, both of which are ethoxylated nonylphenols from Alkaril Chemicals; Surfonic N-40, with an HLB of 8.9, an ethoxylated nonylphenol from Huntsman. See, *McCutcheon's Emulsifiers and Detergents* (1987), especially page 282, incorporated herein by reference thereto. The nonionic surfactant can be chosen from, among others: Alfonic surfactants, sold by Conoco, such as Alfonic 1412-60, a $C_{12-14}$ ethoxylated alcohol with 7 moles of EO; Neodol surfactants, sold by Shell Chemical Company, such as Neodol 25-7, a $C_{12-15}$ ethoxylated alcohol with 7 moles of EO, Neodol 45-7, a $C_{14-15}$ ethoxylated alcohol with 7 moles of EO, Neodol 23-5, a linear $C_{12-13}$ alcohol ethoxylate with 5 moles of EO, HLB of 10.7; Surfonic surfactants, also sold by Huntsman Chemical Company, such as Surfonic L12-6, a $C_{10-12}$ ethoxylated alcohol with 6 moles of EO and L24-7, a $C_{12-14}$ ethoxylated alcohol with 7 moles of EO; and Tergitol surfactants, both sold by Union Carbide, such as Tergitol 25-L-7, a $C_{12-15}$ ethoxylated alcohol with 7 moles of EO, and Tergitol S-15-7, a $C_{11-15}$ ethoxylated alcohol with 7 moles of EO. Macol NP-6, an ethoxylated nonylphenol with 6 moles of EO, and an HLB of 10.8, Macol NP-9.5, an ethoxylated nonylphenol with about 11 moles EO and an HLB of 14.2, Macol NP-9.5, an ethoxylated nonylphenol with about 9.5 moles EO and an HLB of 13.0, both from Mazer Chemicals, Inc.; Triton N-101, an ethoxylated nonylphenol with 9–10 moles of ethylene oxide per mole of alcohol ("EO") having a hydrophile-lipophile balance ("HLB") of 13.4, Triton N-111, an ethoxylated nonylphenol with an HLB of 13.8, both from Rohm & Haas Co.; Igepal CO-530, with an HLB of 10.8, Igepal CO-730, with an HLB of 15.0, Igepal CO-720, with an HLB of 14.2, Igepal CO-710, with an HLB of 13.6, Igepal CO-660, with an HLB of 13.2, Igepal CO-620, with an HLB of 12.6, and Igepal CO-610 with an HLB of 12.2, all polyethoxylated nonylphenols from GAF Chemicals Corp.; Alkasurf NP-6, with an HLB of 11.0, Alkasurf NP-15, with an HLB of 15, Alkasurf NP-12, with an HLB of 13.9, Alkasurf NP-11, with an HLB of 13.8, Alkasurf NP-10, with an HLB of 13.5, Alkasurf NP-9, with an HLB of 13.4, and Alkasurf NP-8, with an HLB of 12.0, all polyethoxylated nonylphenols from Alkaril Chemicals; and Surfonic N-60, with an HLB of 10.9, and Surfonic N-120, with an HLB of 14.1, Surfonic N-102, with an HLB of 13.5, Surfonic N-100, with an HLB of 13.3, Surfonic N-95, with an HLB of 12.9, and Surfonic N-85, with an HLB of 12.4, all polyethoxylated nonylphenols from Huntsman.

The glycosides, particularly the alkyl polyglycosides, may also be used as a surfactant for purposes of the aerosol formulation of the present invention. These glycosides include those of the formula:

$$RO(C_nH_{2n}O)_y(Z)_x$$

wherein R is a hydrophobic group (e.g., alkyl, aryl, alkylaryl etc., including branched or unbranched, saturated and unsaturated, and hydroxylated or alkoxylated members of the foregoing, among other possibilities) containing from about 6 to about 30 carbon atoms, preferably from about 8 to about 15 carbon atoms, and more preferably from about 9 to about 13 carbon atoms; n is a number from 2 to about 4, preferably 2 (thereby giving corresponding units such as ethylene, propylene and butylene oxide); y is a number having an average value of from 0 to about 12, preferably 0; Z is a moiety derived from a reducing saccharide containing 5 or 6 carbon atoms (e.g., a glucose, fructose, mannose, galactose, talose, gulose, allose, altrose, idose, arabinose, xylose, lyxose, or ribose unit, etc., but most preferably a glucose unit); and x is a number having an average value of from 1 to about 10, preferably from 1 to about 5, and more preferably from 1 to about 3.

It would be apparent that a number of variations with respect to the makeup of the glycosides are possible. For example, mixtures of saccharide moieties (Z) may be incorporated into polyglycosides. Also, the hydrophobic group (R) can be attached at the 2-, 3-, or 4-positions of a saccharide moiety rather than at the 1-position (thus giving, for example, a glucosyl as opposed to a glucoside). In addition, normally free hydroxyl groups of the saccharide moiety may be alkoxylated or polyalkoxylated. Further, the $(C_nH_{2n}O)_y$ group may include ethylene oxide and propylene oxide in random or block combinations, among a number of other possible variations.

An exemplary glycoside surfactant is APG 325n, which is manufactured by the Henkel Corporation. APG 325n is a nonionic alkyl polyglycoside in which R is a mixture of $C_9$, $C_{10}$ and $C_{11}$ chains in a weight ratio respectively of 20:40:40 (equivalent to an average of $C_{10.2}$), with x of 1.6, and an HLB of 13.1.

The amine oxides, referred to as mono-long chain, di-short chain, trialkyl amine oxides, have the general configuration:

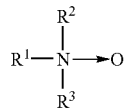

wherein $R^1$ is $C_{6-24}$ alkyl, and $R^2$ and $R^3$ are both $C_{1-4}$ alkyl, or $C_{1-4}$ hydroxyalkyl, although $R^2$ and $R^3$ do not have to be equal. These amine oxides can also be ethoxylated or propoxylated. The preferred amine oxide is lauryl amine oxide. The commercial sources for such amine oxides are Barlox 10, 12, 14 and 16 from Lonza Chemical Company, Varox by Witco and Ammonyx by Stepan Company.

A further semi-polar nonionic surfactant is alkylamidoalkylenedialkyl-amine oxide. Its structure is shown below:

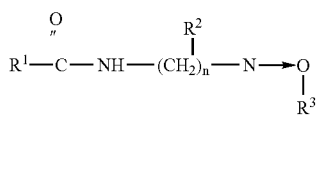

wherein $R^1$ is $C_{5-20}$ alkyl, $R^2$ and $R^3$ are $C_{1-4}$ alkyl, $R^1$—C—NH—$(CH_2)_n$— or —$(CH_2)_p$—OH, although $R^2$ and $R^3$ do not have to be equal or the same substituent, and n is 1–5, preferably 3, and p is 1–6, preferably 2–3. Additionally, the surfactant could be ethoxylated (1–10 moles of EO/mole) or propoxylated (1–10 moles of PO/mole). This surfactant is available from various sources as a cocoamidopropyldimethyl amine oxide; it is sold by Lonza Chemical Company under the brand name Barlox C. Additional semi-polar surfactants may include phosphine oxides and sulfoxides.

In some applications, such as when an aerosol version of the formulation is contemplated, there may be a need to add a defoamer, or to judiciously select a surfactant, or blend of surfactants, which will eliminate or mitigate any undesirable foaming.

It is possible that other surfactants may be suitable for use herein: anionic surfactants, such as, without limitation, alkali metal alkyl sulfates, alkylarylsulfonates, primary and secondary alkane sulfonates (also referred to as paraffin sulfonates), alkyl diphenyloxide disulfonates, and mixtures thereof; cationic surfactants, such as, without limitation, quaternary ammonium, imidazolinium, morpholinium, and other such surfactants; amphoteric surfactants, such as, without limitation, an alkylbetaine, an amidobetaine (especially alkylpropylamidodialkylbetaines, eg., Velvetex AB, from Henkel KGaA), or a sulfobetainedialkylbetaines; and zwitterionic surfactants can be found described in Jones, U.S. Pat. No. 4,005,029, at columns 11–15, which are incorporated herein by reference.

The amount of the surfactants is generally between about 0.1 to about 5%, of the aqueous composition.

b. Fragrances

Fragrances, which are usually lipophilic oils, such as, without limitation, materials which can also function as solvents, such as terpenes and their derivatives, Representative examples for each of the above classes of terpenes with functional groups include but are not limited to the following: Terpene alcohols, including, for example, cis-2-pinanol, pinanol, thymol, 1,8-terpin, dihydro-terpineol, tetrahydro-myrcenol, tetrahydrolinalool, and tetrahydro-alloocimenol; and terpene ethers, including, for example, benzyl isoamyl ether, 1,8-cineole, 1,4-cineole, isobornyl methylether, methyl hexylether. Further, other tertiary alcohols are useful herein. Additional useful solvents include alicyclic hydrocarbons, such as methylcyclohexane. Terpene hydrocarbons with functional groups which appear suitable for use in the present invention are discussed in substantially greater detail by Simonsen and Ross, *The Terpenes*, Volumes I–V, Cambridge University Press, 2nd Ed., 1947 (incorporated herein by reference thereto). See also, co-pending and commonly assigned Choy, U.S. Pat. No. 5,279,728, incorporated herein by reference thereto. Other fragrances are found amongst combinations of aldehydes, esters, essential oils, and the like. See, Bertrand et al., U.S. Pat. No. 4,938,416, Swatling et al, U.S. Pat. No. 5,227,366, Schleppnik et al., U.S. Pat. No. 4,009,253, Berger, U.S. Pat. No. 4,137,251, and Schleppnik, U.S. Pat. Nos. 4,310,512 and 4,622,221, all of which are incorporated herein by reference. Fragrances are available from such vendors as Givaudan-Rohre, International Flavors and Fragrances, Firmenich, Norda, Bush Boake and Allen, Quest and others.

c. Dyes and Colorants

Dyes and colorants which can be solubilized or suspended in the formulation. A wide variety of dyes or colorants can be used to impart an aesthetically and commercially pleasing appearance. The amounts of these aesthetic adjuncts should be in the range of 0–2%, more preferably 0–1%.

d. Antimicrobials

Additionally, because the surfactants in liquid systems are sometimes subject to attack from microorganisms, it is advantageous to add a preservative, i.e., mildewstat or bacteristat. Exemplary mildewstats (including non-isothiazolone compounds) include Kathon GC, a 5-chloro-2-methyl-4-isothiazolin-3-one, Kathon ICP, a 2-methyl-4-isothiazolin-3-one, and a blend thereof, and Kathon 886, a 5-chloro-2-methyl-4-isothiazolin-3-one, all available from Rohm and Haas Company; Bronopol, a 2-bromo-2-nitropropane 1,3-diol, from Boots Company Ltd.; Proxel CRL, a propyl-p-hydroxybenzoate, from ICI PLC; Nipasol M, an o-phenyl-phenol, Na+ salt, from Nipa Laboratories Ltd.; Integra 44 (a sodium hydroxymethylglycinate) from ISP; Dowicide A, a 1,2-benzoisothiazolin-3-one, from Dow Chemical Co.; and Irgasan DP 200, a 2,4,4'-trichloro-2-hydroxy-diphenylether, from Ciba-Geigy A.G. See also, Lewis et al., U.S. Pat. No. 4,252,694 and U.S. Pat. No. 4,105,431, incorporated herein by reference. Other actives include, without limitation, quaternary ammonium compounds, "polyquats," which are reaction products/mixtures of anionic polymer or prepolymers with quaternary ammonium compounds, phenols, 3-isothiazolones, methyl and propyl parabens, and the like. These antimicrobial materials may be desirable to be delivered to a particular surface, such as fabrics, or hard surfaces, so as to deliver residual antimicrobial activity. Especially preferred are the polyquats which are referred to in Zhou, U.S. patent application Ser. No. 08/833,276, filed Apr. 4, 1997, and Zhou et al., U.S. patent application Ser. No. 09/116,190, filed Jul. 15, 1998, both of common assignment, and incorporated herein by reference thereto.

e. Miscellaneous Adjuncts

Small amounts of adjuncts can be added for improving aesthetic qualities of the invention. Other desirable additives may include chelating agents (without limitation, such as alkali metal salts of EDTA, preferably tetrapotassium EDTA; See Robbins et al., U.S. Pat. No. 5,972,876, incorporated herein by reference; or tetraammonium EDTA; see Mills et al., U.S. Pat. No. 5,814,591, incorporated herein by reference) salts, pigments, colorants and the like. Additional surfactants (anionic, nonionic, cationic, amphoteric, zwitterionic and mixtures), hydrotropes, solvents, and other dispersing aids may also be added in discrete amounts, taking into account their individual performance attributes and whether their addition may affect the product stability.

In the following Experimental section, examples of the inventive composition are provided.

EXPERIMENTAL

In the following section, examples of various embodiments of the invention are depicted. Where ingredients are repeated in some of the Examples, and have been previously identified in footnotes in prior Examples, those footnotes are not repeated.

EXAMPLE I

Aqueous Liquid Pet Malodor Mitigating Composition

| Ingredient | Weight % |
|---|---|
| Deionized Water[1] | 90.70 (q.s. to 100%) |
| Acrylic Polymer Emulsion[2] | 1.08 |
| Ethanol[3] | 5.00 |
| Polyether modified Polydimethylsiloxane[4] | 0.03 |
| Preservative[5] | 0.10 |
| Nonionic Surfactant[6] | 0.50 |
| Fragrance[7] | 0.20 |
| Dipotassium tetraborate decahydrate[8] | 0.70 |
| Total: | 100.00% |

[1]May not necessarily need to be deionized
[2]Carboset polymer, B F Goodrich
[3]Solvent, Mid West Grain
[4]BYK Chemie
[5]Integra
[6]Union Carbide.
[7]Bush Boake and Allen.
[8]U.S. Borax These ingredients are merely admixed together, with gentle stirring. The preferred order of addition is to disperse the fragrance via the surfactant and to neutralize the polymer (although one can purchase versions that are already neutralized. So, to disperse the fragrance adequately, a preblend of water, surfactant and fragrance, and then this preblend is added to the bulk of the product. The finished liquid pet malodor mitigating composition can then be loaded into trigger or pump sprayers. It may also be possible to load them into cans for aerosol delivery. However, cost, the presence of an additional solvent (the propellant) and the ensuing reduction in water content, are considerations in aerosol delivery. If aerosol delivery is practiced, there are preferred systems described in co-pending patent application Ser. No. 09/116,190, of Boli Zhou et al, filed Jul. 15, 1998, and incorporated herein by reference. Preferably, but by no means limiting to the invention, the composition is delivered in a trigger sprayer made of high density polyethylene (HDPE) or polypropylene, although it is desirable to use transparent polyvinyl chloride (PVC) or, especially, polyethylene terphthalate (PET), and other transparent or translucent thermopolymers. Examples of such sprayers are depicted in Hefter et al., U.S. D-404,650, Bolliger et al., U.S. D-401,504, and Malmquist, U.S. D-372,428, all of which are incorporated herein by reference.

In application, a fine spray or mist is applied to a surface having the waste(s) giving rise to the malodor thereon. It has been determined that after the waste(s) have been wetted, and then allowed to dry, the waste(s) are thus entrapped in the minute, transparent residue or film, said film containing the borax active. This has been observed to be especially effective at malodor mitigation or elimination. Because the quantity of product used is very sparing, the invention presents an extremely cost-effective solution to the elimination or mitigation of these particularly noxious malodors in enclosed living, working and gathering spaces.

EXAMPLE 2

Cat Litter Deodorizer Test

In this test, the inventive malodor counteractant was blind tested on soiled litter boxes to demonstrate the efficacy of the invention. This test was meant to assay not only immediate odor control, but residual odor control as well.

In the test, full sized cat litter boxes which have been preinnoculated with a standard amount of cat urine are evaluated by an expert panel of about 30 in-house panelists on a 0 to 60 scale, with 60 being the highest in malodor. These boxes are, over time, additionally re-soiled with additional liquid and solid cat wastes to replicate the domestic animal's standard pattern of elimination. No to low odor typically is scaled at a score of below 15, while high malodor is from 35–50. This was a blind test, meaning the samples were unlabeled so the panelists were not influenced by the identity of the product tested.

In the test, the invention (which, in FIG. 1, is labeled the POP Prototype and is the darker of the two bars) significantly outperformed the control, which is a commercially available surface deodorizer and is labeled Control, the lighter of the two bars) over a period of up to 76 hours. The results are depicted in FIG. 1.

EXAMPLE 3

Cat Spray Deodorizing Tests

Figure 2:
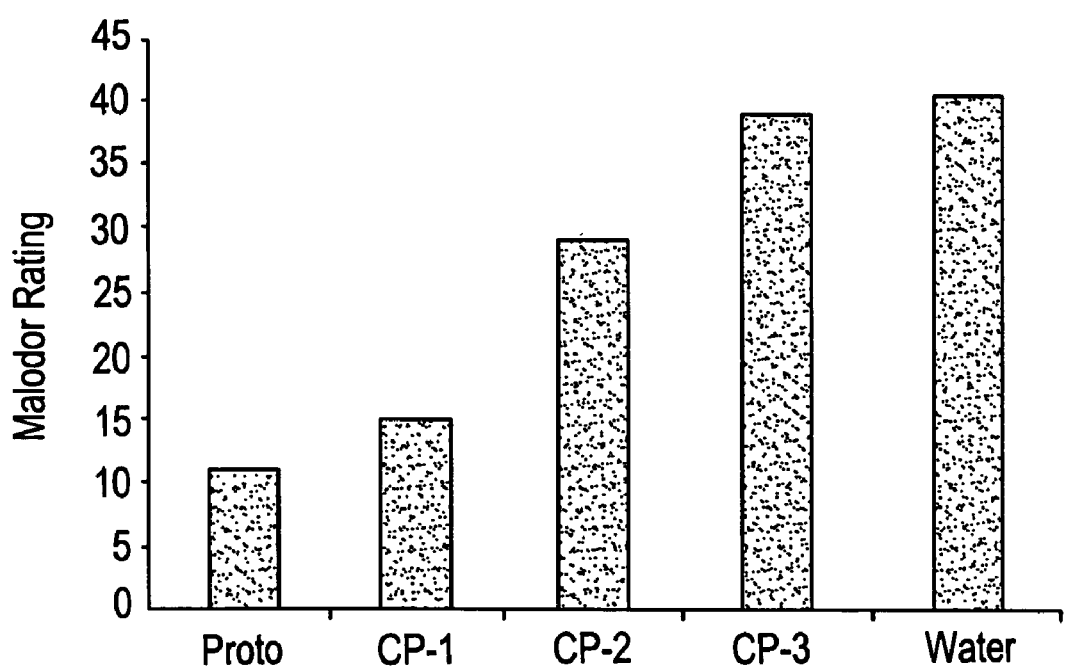
FIG. 2 is bar graph depicting the performance of the invention versus commercially available surface deodorizers and water (as a control).

In this next experiment, the effect of the inventive product against Cat Spray, which again is the finely divided spray cats produce (mostly constituted of urine) which cats use to mark territory, is considered. Consumers have identified Cat Spray as one of the strongest and most difficult odors to remove. In this test, to simulate cats marking, fabric (upholstery) swatches were used to test efficacy of both the invention and a number of commercially available surface deodorizers and water. These swatches, being of standardized sizes, can be dosed with a consistent amount of a simulated cat spray (an artificial cat spray developed internally by sensory experts, which was created by using pooled cat urine), which is applied to the swatches according to a specially developed protocol. Generally speaking, the simulated cat spray is dosed by a specialized doser. The innoculated swatches are then stored in standardized plastic covered containers and left at room temperature for up to one week or until ready to be tested. Prior to evaluation, the containers are opened and left open over night. Prior to sensory evaluation, the swatches are removed from the containers and treated with, respectively, the invention, the commercial products and water (as a control), in a standardized amount of about less than 3 grams of products each. A group of expert panelists again rated each swatch according to a 0 to 60 scale. Again, this was a blind test. In the time frame of assessment (about 48 hours), it was determined that the invention (labeled "Proto") in the bar graph of FIG. 2 was numerically superior to each the remaining commercial products (labeled CP1, CP2 and CP3) and water (Control). The results are depicted in FIG. 2 graphically.

EXAMPLE 4

Comparison of Ammonia Generation

Figure 3:
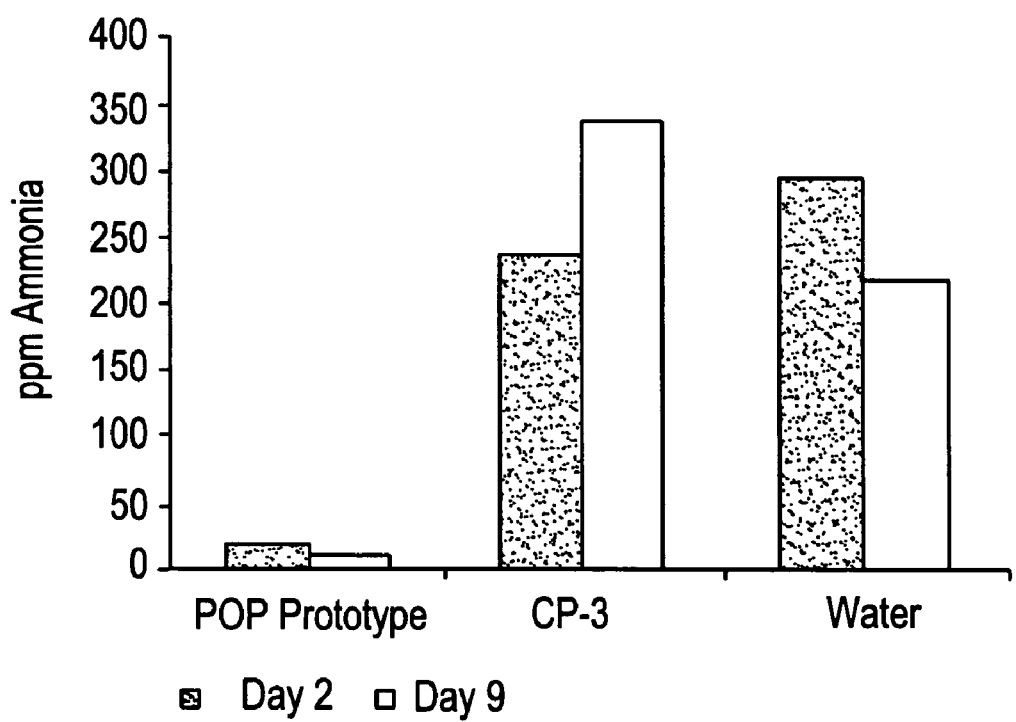
FIG. 3 is a bar graph demonstrating the performance of the invention in combating ammonia production from cat spray swatches versus a commercially available surface deodorizer and water (as a control).

In this test, saturation of swatches in accordance with the directions of one particular competitive product was tested. The products tested were the invention, the competitive product CP-3 and water (as a control). The times tested were after 48 hours (2 days) and 216 hours (9 days) incubation at room temperature (70° F., 21° C.). The ammonia generation was determined by using a Kitegawa toxic gas detector with Matheson ammonia detector tubes. Naturally, a score that is higher in ppm $NH_3$ is less preferred. In this test, the invention, labeled POP Prototype, vastly outperformed both CP-3 and water. The results are depicted in FIG. 3.

EXAMPLE 5

In the next example, an aerosolized version of the inventive malodor composition is provided:

| Ingredient | Wt. % | Name |
|---|---|---|
| Propellant | 27.5% | Dimethylether |
| Polymer | 2.00% | Acrylic Polymer Emulsion |
| Solvent | 8.0% | Ethanol |
| Nonionic Surfactant | 0.50% | Tergitol |
| Corrosion Inhibitors | 1.9% | Various |
|  | 0.70% | Sodium Borax |
| Water | q.s. |  |

The invention is further defined without limitation of scope by the claims which follow hereto.

The invention claimed is:

1. A product for mitigating or eliminating pet malodor(s) on surfaces to which the malodors have been applied, the product consisting essentially of: an aqueous liquid deodorizing composition, the composition containing about at least 0.01% to about 10% of a dialkali metal tetraborate n-hydrate wherein n is an interger from 0 to 10, 0.1–3% water dispersible acrylic emulsion polymer having an acid number from about 75–500 and an average molecular weight of about 500–20,000, 1–25% water soluble/dispersible volatile solvent, and at least 75% water.

2. The product of claim 1 wherein said malodor(s) are from ammonia formation due to decomposition of urea present in animal waste.

3. The method for the mitigation of pet malodor(s) on surfaces comprising contacting said malodor(s) with an aqueous liquid deodorizing composition wherein the malodor(s) are from ammonia formation due to decomposition of urea present in animal waste, and wherein the composition consisting essentially of: about at least 0.01% to about 10% of a dialkali metal tetraborate n-hydrate wherein n is an interger from 0 to 10, 0.1–3% water dispersible acrylic emulsion polymer having an acid number from about 75–500 and an average molecular weight of about 500–20,000, 1–25% water soluble/dispersible volatile solvent, and at least 75% water.

4. The method of claim 3 wherein said composition further comprises at least one aesthetic and/or functional additive.

5. The method of claim 3 wherein said dialkali metal tetraborate n-hydrate is selected from the group consisting of borax pentahydrate and borax decahydrate.

6. The method of claim 3 wherein said solvent is selected from the $C_{1-6}$ alkanols and $C_{1-24}$ glycol ethers.

* * * * *